United States Patent
Kaufman et al.

(10) Patent No.: US 8,382,809 B2
(45) Date of Patent: Feb. 26, 2013

(54) POLY-AXIAL PEDICLE SCREW IMPLEMENTS AND LOCK SCREW THEREFOR

(75) Inventors: Kevin Kaufman, Ft. Worth, TX (US); Jamie Gottlieb, Granger, IN (US); Douglas Won, Dallas, TX (US); Michael Rimlawi, Dallas, TX (US)

(73) Assignee: Omni Surgical, Austin, TX (US)

( * ) Notice: Subject to any disclaimer, the term of this patent is extended or adjusted under 35 U.S.C. 154(b) by 737 days.

(21) Appl. No.: 12/288,184

(22) Filed: Oct. 17, 2008

(65) Prior Publication Data
US 2010/0100136 A1 Apr. 22, 2010

(51) Int. Cl.
*A61B 17/68* (2006.01)

(52) U.S. Cl. ......... 606/305; 606/246; 606/264; 606/270

(58) Field of Classification Search .................. 606/272, 606/246, 264, 270, 305; 411/303
See application file for complete search history.

(56) References Cited

U.S. PATENT DOCUMENTS

| | | | |
|---|---|---|---|
| 2,354,160 A * | 7/1944 | Wallgren | ...................... 411/393 |
| 2,355,899 A | 8/1944 | Beede | |
| 4,946,458 A | 8/1990 | Harms | |
| 5,207,678 A | 5/1993 | Harms | |
| 5,344,422 A | 9/1994 | Frigg | |
| 5,474,555 A * | 12/1995 | Puno et al. | ..................... 606/266 |
| 5,474,558 A | 12/1995 | Neubardt | |
| 5,520,689 A | 5/1996 | Schlapfer | |
| 5,669,911 A | 9/1997 | Errico | |
| 6,016,727 A * | 1/2000 | Morgan | ........................... 81/436 |
| 6,053,917 A | 4/2000 | Sherman | |
| 6,296,642 B1 * | 10/2001 | Morrison et al. | ............. 606/305 |
| 6,368,319 B1 | 4/2002 | Schaefer | |
| 6,402,752 B2 | 6/2002 | Schaffler-Wachter | |
| 6,485,494 B1 * | 11/2002 | Haider | .......................... 606/302 |
| 6,488,681 B2 * | 12/2002 | Martin et al. | .................. 606/278 |
| 6,565,565 B1 | 5/2003 | Yuan | |
| 6,565,567 B1 | 5/2003 | Haider | |
| 6,652,926 B1 * | 11/2003 | Takada et al. | .................. 428/1.2 |
| 6,660,004 B2 | 12/2003 | Barker | |
| 6,755,829 B1 * | 6/2004 | Bono et al. | ..................... 606/308 |
| 6,989,011 B2 | 1/2006 | Paul | |
| 7,066,937 B2 | 6/2006 | Shluzas | |
| 7,081,116 B1 * | 7/2006 | Carly | ............................. 606/264 |
| 7,087,057 B2 | 8/2006 | Konieczynski | |
| 7,144,396 B2 * | 12/2006 | Shluzas | ......................... 606/266 |
| 7,207,992 B2 | 4/2007 | Ritland | |
| 7,220,262 B1 | 5/2007 | Hynes | |
| 7,306,606 B2 * | 12/2007 | Sasing | ............................ 606/279 |
| 7,604,656 B2 * | 10/2009 | Shluzas | ......................... 606/270 |

(Continued)

*Primary Examiner* — Thomas J Sweet
*Assistant Examiner* — Seema Mathew
(74) *Attorney, Agent, or Firm* — David O. Simmons

(57) ABSTRACT

A lock screw assembly for use with a pedicle screw assembly comprises a lock screw and an upper saddle. The lock screw includes a fastening tool engaging structure at a first end portion thereof and an upper saddle receiving structure at a second end portion thereof. The upper saddle is engaged with the upper saddle receiving structure of the lock screw in a manner allowing the upper saddle to rotate about a centerline axis of the lock screw. A plurality of intersecting spine rod receiving channels extend through a spine rod engaging portion of the upper saddle in a manner such that an outwardly-extending spine rod engaging structure is provided between adjacent ones of the spine rod receiving channels. Upper and lower surfaces of each spine rod engaging structure are acutely angled with respect to each other and wherein a channel edge defined between the surfaces is sharply pointed.

3 Claims, 4 Drawing Sheets

U.S. PATENT DOCUMENTS

| | | |
|---|---|---|
| 7,625,394 B2 * | 12/2009 | Molz et al. .................... 606/270 |
| 7,678,139 B2 | 3/2010 | Garamszegi |
| 7,828,829 B2 * | 11/2010 | Ensign ......................... 606/305 |
| 7,867,257 B2 * | 1/2011 | Na et al. ....................... 606/266 |
| 7,867,258 B2 * | 1/2011 | Drewry et al. ................ 606/266 |
| 8,308,782 B2 * | 11/2012 | Jackson ........................ 606/308 |
| 2002/0143341 A1 | 10/2002 | Biedermann |
| 2003/0004512 A1 * | 1/2003 | Farris et al. ..................... 606/61 |
| 2003/0100896 A1 | 5/2003 | Biedermann |
| 2003/0100904 A1 * | 5/2003 | Biedermann ................... 606/73 |
| 2005/0283157 A1 * | 12/2005 | Coates et al. ................... 606/73 |
| 2006/0161153 A1 | 7/2006 | Hawkes |
| 2008/0221621 A1 * | 9/2008 | Snyder et al. ................. 606/263 |
| 2008/0249570 A1 * | 10/2008 | Carson et al. ................. 606/264 |
| 2008/0262548 A1 * | 10/2008 | Lange et al. .................. 606/256 |
| 2011/0270321 A1 * | 11/2011 | Prevost et al. ................ 606/305 |
| 2012/0004689 A1 * | 1/2012 | Biedermann et al. ......... 606/305 |
| 2012/0059427 A1 * | 3/2012 | Schlapfer ...................... 606/305 |
| 2012/0143260 A1 * | 6/2012 | Gunn et al. ................... 606/302 |

* cited by examiner

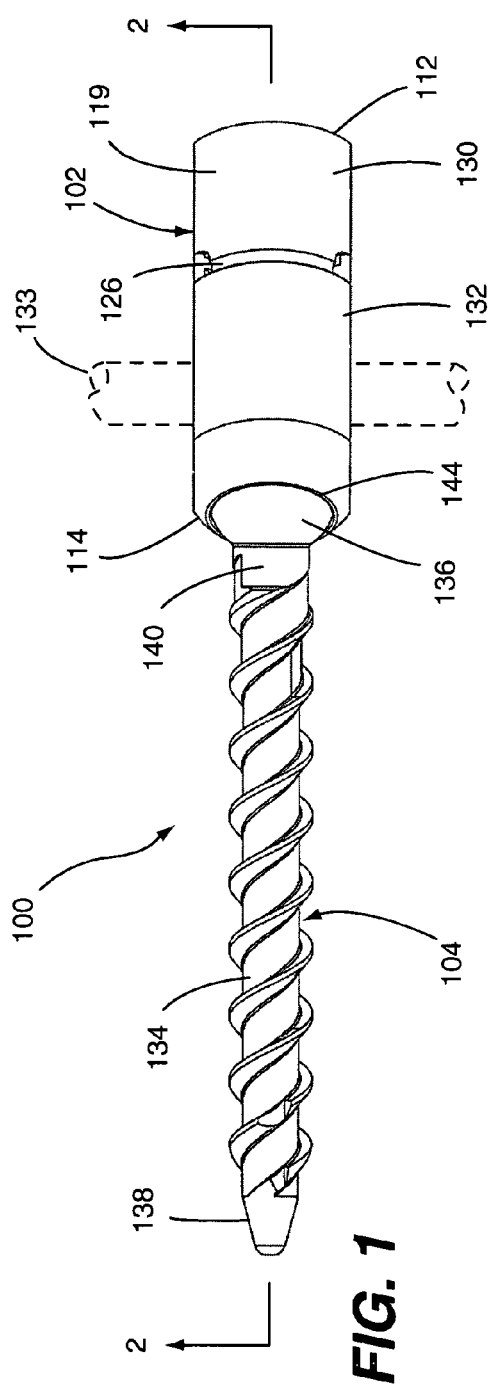
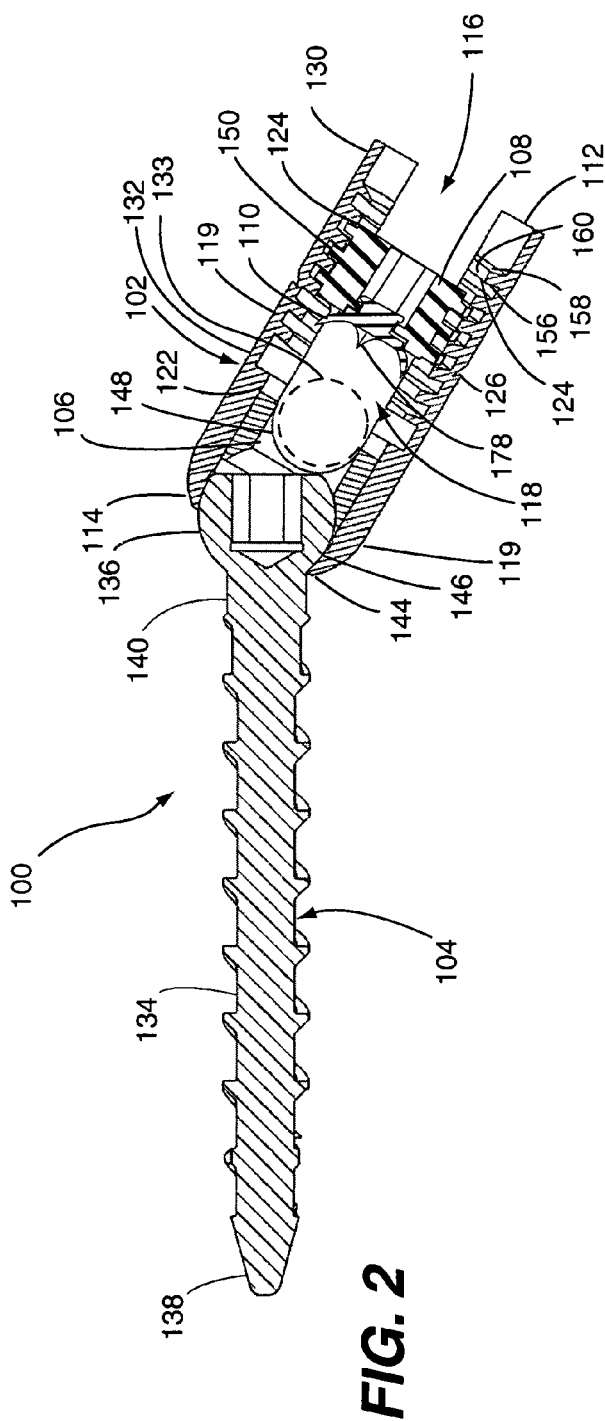
FIG. 1
FIG. 2

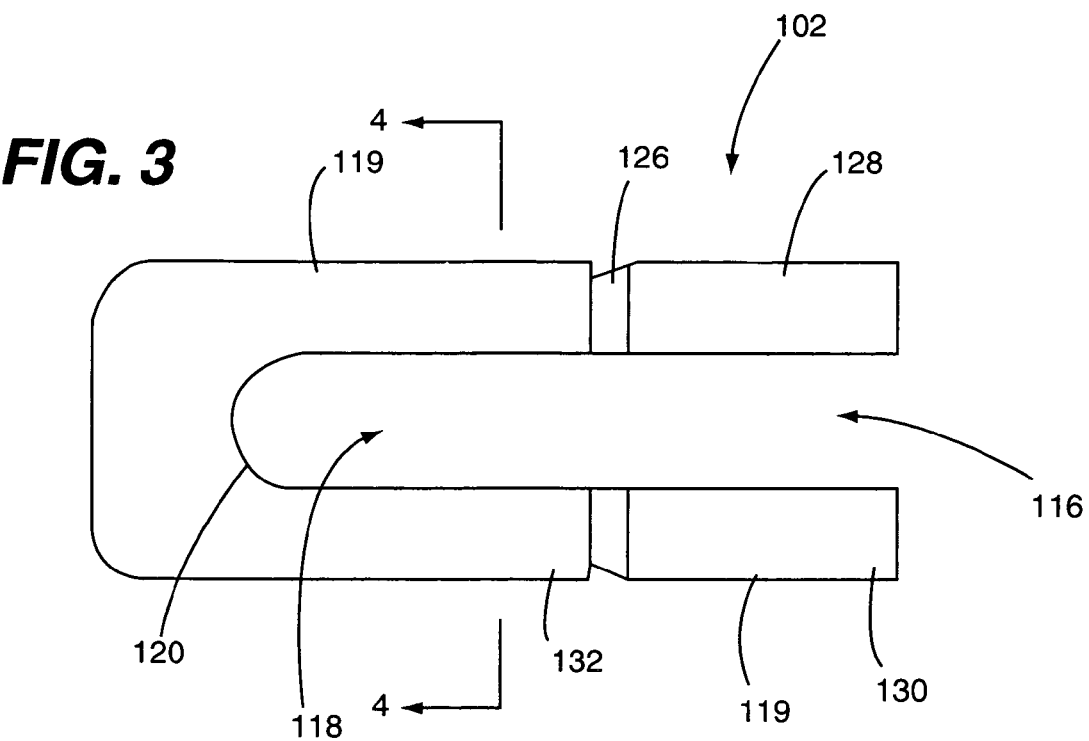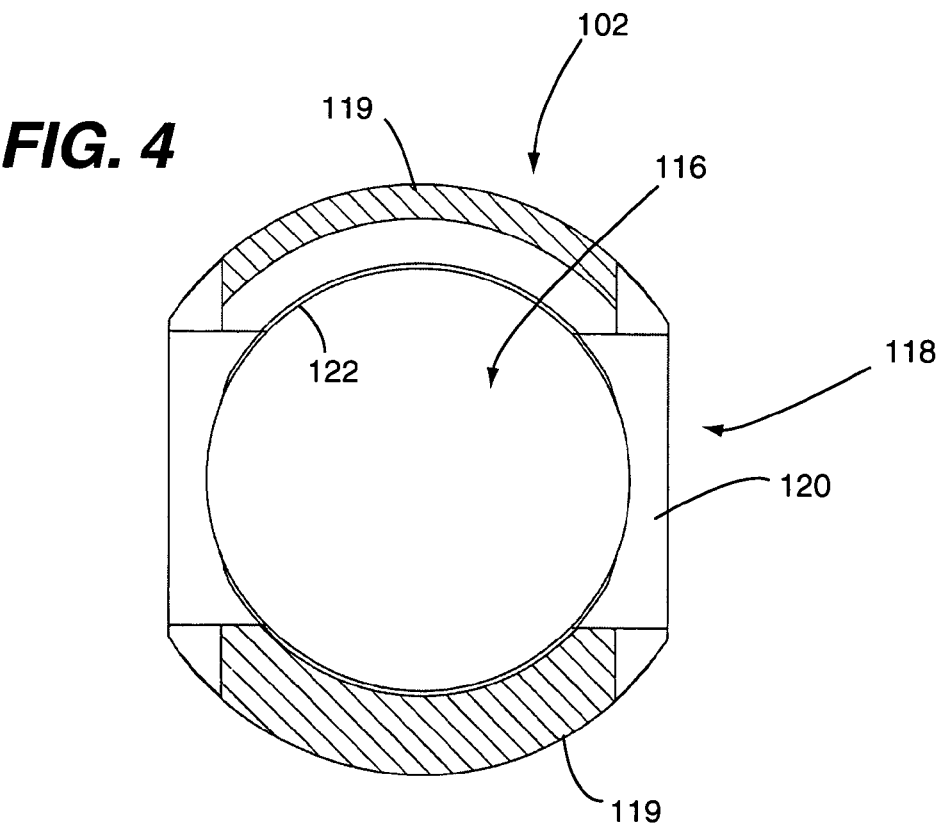

POLY-AXIAL PEDICLE SCREW IMPLEMENTS AND LOCK SCREW THEREFOR

FIELD OF THE DISCLOSURE

The disclosures made herein relate generally to pedicle screw assemblies and, more particularly, to saddle configurations of poly-axial pedicle screw assemblies.

BACKGROUND

The spinal column is a highly complex system of bones (i.e., vertebral bodies) and connective tissues that provides support for the body and protects the delicate spinal cord and nerves. The spinal column includes a series of vertebrae stacked one atop the other, each vertebral body including an inner or central portion of relatively weak cancellous bone and an outer portion of relatively strong cortical bone. Situated between each vertebral body is an intervertebral disc that cushions and dampens compressive forces on the spinal column. A vertebral canal containing the spinal cord and nerves is located within the forward-facing surface of the vertebral bodies.

There are many types of spinal column disorders. Patients that suffer from such disorders typically experience extreme and debilitating pain, as well as diminished nerve function. Examples of such spinal column disorders include, but are not limited to, scoliosis (i.e., abnormal lateral curvature of the spine), kyphosis (i.e., abnormal forward curvature usually in the thoracic portion of the spine), excess lordosis (i.e., abnormal backward curvature usually in the lumbar portion of the spine), spondylolisthesis (forward displacement of one vertebrae over another usually in the lumbar portion or cervical portion of the spine), etc. There are still other types of spinal column disorders caused by physiological abnormalities, disease and/or trauma such as, for example, ruptured or slipped discs, degenerative disc disease, fractured vertebra, and the like.

Multi-segmental spinal fixation is an accepted surgical procedure in the treatment of such spinal column disorders. It involves the use of a series of pedicle screw assemblies and one or more spine rods. The pedicle screw assemblies each include a screw that is threadedly screwed into one of a plurality of adjacent vertebral bodies. A spine rod (contoured or straight) is fixedly secured to a spine rod clamping body of each one of the pedicle screws for fixing two or more adjacent vertebral bodies in a static relative position. In this manner, spinal fixation can be used to alter the alignment of adjacent vertebrae relative to one another so as to change the overall alignment of the spine, to preclude relative movement between adjacent vertebrae, and the like.

The effectiveness of multi-segmental spinal fixation is dependant on several considerations. Examples of such considerations include, but are not limited to, the ability of a pedicle screw assembly to readily and rigidly accommodate a spine rod bent to the contour of the spine, the ability of a pedicle screw assembly to reliably secure the bent spine rod in a fixed position and orientation, the ability of a screw of a pedicle screw assembly to be threadedly engaged with a vertebral body in a manner that provides acceptable mechanical strength, and the ability of a screw of a pedicle screw assembly to be threadedly engaged with a vertebral body in a manner that minimized adverse deformation and/or damage to the vertebral body. Known pedicle screw assemblies are deficient in one or more of these considerations, thus limiting their effectiveness.

Therefore, a pedicle screw apparatus, pedicle screw system and/or a lock screw for use therewith that overcomes deficiencies associated with known pedicle screw implements would be advantageous, desirable and useful.

SUMMARY OF THE DISCLOSURE

Embodiments of the present invention provide for pedicle screw implements (e.g., a pedicle screw apparatus, pedicle screw system and/or a lock screw for use therewith) that overcome one or more deficiencies associated with known pedicle screw implements. More specifically, pedicle screw implements in accordance with embodiments of the present invention advantageously impact the ability of a pedicle screw assembly to readily and rigidly accommodate a spine rod bent to the contour of the spine, the ability of a pedicle screw assembly to reliably secure the bent spine rod in a fixed position and orientation, the ability of a screw of a pedicle screw assembly to be threadedly engaged with a vertebral body in a manner that provides superior mechanical strength, and/or the ability of a screw of a pedicle screw assembly to be threadedly engaged with a vertebral body in a manner that minimized adverse deformation and/or damage to the vertebral body. In doing so, embodiments of the present invention advantageously impact the implementation and resulting effectiveness of multi-segmental spinal fixation.

In one embodiment of the present invention, a lock screw assembly for use with a pedicle screw assembly comprises a lock screw and an upper saddle. The lock screw includes a fastening tool engaging structure at a first end portion thereof and an upper saddle receiving structure at a second end portion thereof. The upper saddle is engaged with the upper saddle receiving structure of the lock screw in a manner allowing the upper saddle to rotate about a centerline axis of the lock screw. A plurality of intersecting spine rod receiving channels extend through a spine rod engaging portion of the upper saddle in a manner such that an outwardly-extending spine rod engaging structure is provided between adjacent ones of the spine rod receiving channels. Upper and lower surfaces of each spine rod engaging structure are acutely angled with respect to each other and wherein a channel edge defined between the surfaces is sharply pointed.

In another embodiment of the present invention, a pedicle screw system comprises a clamping body and a lock screw assembly. The clamping body includes an axial passage extending between a first end portion and a second end portion thereof and a spine rod receiving channel extending through the first end portion of the clamping body in a traverse direction with respect to the axial passage. A closed end portion of the spine rod receiving channel is located between the end portions of the clamping body. A surface of the clamping body defining the axial passage has threads formed therein. The clamping body threads are cupped upwardly toward the first end portion of the clamping body. The lock screw assembly includes a lock screw and an upper saddle. The lock screw is configured for being disposed within the axial passage of the clamping body with threads thereof matingly engaged with the clamping body threads. The lock screw includes a fastening tool engaging structure at a first end portion thereof and an upper saddle receiving structure at a second end portion thereof. The lock screw threads are cupped upwardly toward the first end portion of the lock screw. The upper saddle is engaged with the upper saddle receiving structure of the lock screw in a manner allowing the upper saddle to rotate about a centerline axis of the lock screw.

In another embodiment of the present invention, a pedicle screw apparatus comprises a clamping body, a screw, a lower saddle, a lock screw and an upper saddle. The clamping body includes an axial passage extending between a first end portion and a second end portion thereof and a spine rod receiving channel extending through the first end portion of the clamping body in a traverse direction with respect to the axial passage. A closed end portion of the spine rod receiving channel is located between the end portions of the clamping body and a surface of the clamping body defining the axial passage has threads formed therein. The clamping body threads are cupped upwardly toward the first end portion of the clamping body. The screw includes a shaft and a semispherical shaped head attached to an end portion of the shaft. The shaft has bone engaging threads provided along a length thereof. The screw head is secured within the second end portion of the clamping body in a manner that limits axial displacement of the screw in a direction toward the second end portion of the clamping body, that allows pivoting of the clamping body about the screw head and that allows rotation of the clamping body about a longitudinal axis thereof. The lower saddle is disposed within the axial passage proximate the screw head. A screw head engaging surface of the lower saddle has a mating concave contour to the semi-spherical shape of the screw head. A spine rod engaging portion of the lower saddle extends above the closed end portion of the spine rod receiving channel when the screw head engaging surface of the lower saddle is engaged with the screw head thereby allowing relative movement between the screw and the clamping body to be inhibited in response to a spine rod disposed within the spine rod receiving channel forcibly urging the lower saddle against the screw head. The lock screw is configured for being disposed within the axial passage of the clamping body with threads thereof matingly engaged with the clamping body threads. The lock screw includes a fastening tool engaging structure at a first end portion thereof and an upper saddle receiving structure at a second end portion thereof. The lock screw threads are cupped upwardly toward the first end portion of the lock screw. The upper saddle is engaged at a first end portion thereof with the upper saddle receiving structure of the lock screw in a manner allowing the upper saddle to rotate about a centerline axis of the lock screw. Perpendicularly intersecting spine rod receiving channels extend through a spine rod engaging portion of the upper saddle in a manner such that an outwardly-extending spine rod engaging structure is provided between adjacent ones of the spine rod receiving channels. Upper and lower surfaces of each spine rod engaging structure are acutely angled with respect to each other and wherein a channel edge defined between the surfaces is sharply pointed.

These and other objects, embodiments, advantages and/or distinctions of the present invention will become readily apparent upon further review of the following specification, associated drawings and appended claims.

BRIEF DESCRIPTION OF THE DRAWINGS

FIG. 1 is a plan view showing a pedicle screw apparatus in accordance with an embodiment of the present invention.

FIG. 2 is a cross sectional view taken along the line 2-2 in FIG. 1.

FIG. 3 is a side view of a clamping body for a pedicle screw apparatus in accordance with an embodiment of the present invention.

FIG. 4 is a cross sectional view taken along the line 4-4 in FIG. 3.

DETAILED DESCRIPTION OF THE DRAWING FIGURES

Figure 5:
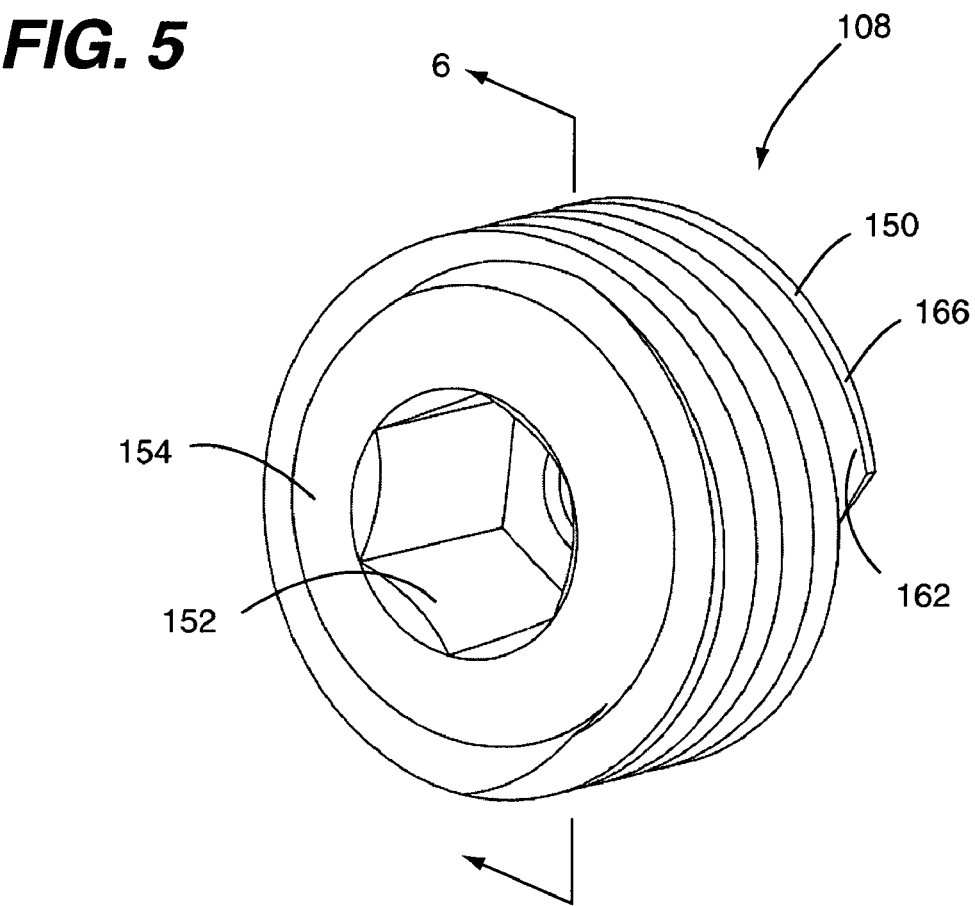
FIG. 5 is a perspective view of a locking screw assembly for a pedicle screw apparatus in accordance with an embodiment of the present invention.

Pedicle screw implements in accordance with embodiments of the present invention are used in performing multi-segmental spinal fixation to alter the alignment of adjacent vertebrae relative to one another so as to change the overall alignment of the spine, to preclude relative movement between adjacent vertebrae, and the like. Advantageously, such pedicle screw implements improve the effectiveness of multi-segmental spinal fixation. Specifically, such pedicle screw implements have a construction that enhances functionality associated with readily and rigidly accommodating a spine rod bent to the contour of the spine, with reliably securing the bent spine rod in a fixed position and orientation, with being threadedly engaged with a vertebral body in a manner that provides superior mechanical strength, and being threadedly engaged with a vertebral body in a manner that minimized adverse deformation and/or damage to the vertebral body. Accordingly, embodiments of the present invention offer functionality and/or structure that is advantageous with respect to known pedicle screw implements.

Referring now to FIGS. 1 and 2, a pedicle screw apparatus 100 in accordance with an embodiment of the present invention is shown. The pedicle screw apparatus 100 includes a clamping body 102, a screw 104, a lower saddle 106, a lock screw 108 and an upper saddle 110. As is discussed below in greater detail, the clamping body 102, the screw 104, the lower saddle 106, the lock screw 108 and the upper saddle 110 are constructed and/or interconnected in a manner that provides advantageous functionality and/or structure with respect to known pedicle screw implements.

Referring to FIGS. 1-3, the clamping body 102 has a first end portion 112 and a second end portion 114. An axial passage 116 (shown in FIG. 2) extends axially (i.e., along a longitudinal axis of he clamping body 102) between the first and second end portions 112, 114. A spine rod receiving channel 118 extending through the first end portion 112 in a traverse direction with respect to the axial passage 116, thus forming upstanding leg portions 119 of the clamping body 102. A closed end portion 120 of the spine rod receiving channel 118 is located between the first and second end portions 112, 114. A surface 122 of the clamping body that defines the axial passage 116 has clamping body threads 124 formed therein.

Reliefs 126 are provided in an outer surface 128 of the upstanding leg portions 119 of the clamping body 102. In view of the reliefs 126, an upper segment 130 of each upstanding leg portion 119 is frangibly detachable from a lower segment 132 thereof. This frangible functionality provides for ease in engaging and securing a spine rod 133 within the clamping body 102 (i.e., with the upper segments 130 still attached) and for a lower profile of the implanted pedicle screw apparatus 100 (i.e., with the upper segments 130 detached).

Referring to FIGS. 1 and 2, the screw 104 includes a shaft 134 and a semi-spherical shaped screw head 136. The shaft 134 includes a tip portion 138 and an upper end portion 140. The screw head 136 is attached to the upper end portion 140 of the shaft 134. The shaft 134 has bone engaging threads 142 provided along a length thereof. Screws in accordance with the present invention are not limited to a particular type of thread. However, double lead threads are a preferred thread for pedicle screw implements in accordance with embodiments of the present invention. With respect to single lead threads, it has been found that double lead threads allow for faster screw insertion while providing for greater pull out strength and increased fatigue strength at the bone-screw interface.

The screw head 136 is secured within the second end portion 114 of the clamping body 102. The screw head 136 is secured in a manner that limits axial displacement of the screw 104 in a direction toward the second end portion 114 of the clamping body 102, that allows pivoting of the clamping body 102 about the screw head 136 and that allows rotation of the clamping body 102 about a longitudinal axis thereof. For example, in one embodiment of the present invention, a tip portion 144 of the second end portion 114 has a mating concave contour to the semi-spherical shape of the screw head 136, thus allowing such relative rotation and pivoting between the clamping body 102 and the screw 104.

Referring to FIG. 2, the lower saddle 106 is slideably disposed within the axial passage 116 proximate the screw head 136. A screw head engaging surface 146 of the lower saddle 106 has a mating concave contour to the semi-spherical shape of the screw head 136. A spine rod engaging portion 148 of the lower saddle 106 (i.e., a generally u-shaped recess) extends above the closed end portion 120 of the spine rod receiving channel 118 when the screw head engaging surface 146 is engaged with the screw head 136. In this manner, relative movement between the screw 104 and the clamping body 102 is allowed prior to a spine rod being forcibly urged against the lower saddle by the lock screw 108 and is inhibited in response to the spine rod 133 disposed within the spine rod receiving channel 118 being forcibly urged against the lower saddle 106 by the lock screw 108 thereby causing the screw head 136 to become clamped between the tip portion 144 of the clamping body 102 and the screw head engaging surface 146 of the lower saddle 106. To further promote such inhibited relative movement, the screw head 136 can include surface texture (e.g., circumferential grooves, rough surface, etc) to enhance friction.

Figure 6:
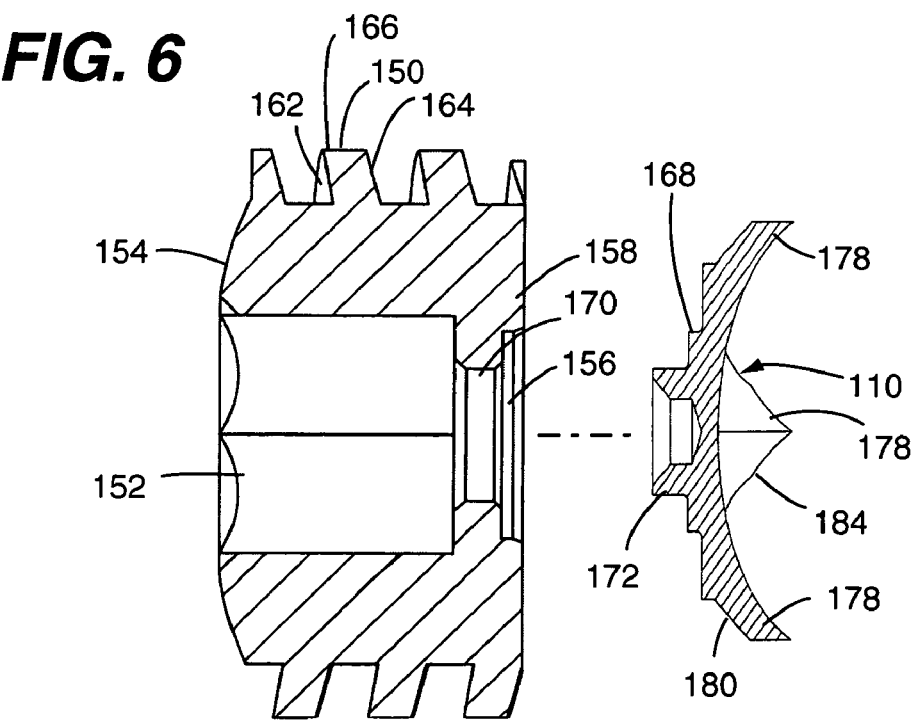
FIG. 6 is an exploded cross sectional view taken along the line 6-6 in FIG. 5.

Referring to FIGS. 2, 5 and 6, the lock screw 108 is configured for being disposed within the axial passage 116 with threads 150 thereof matingly engaged with the clamping body threads 124. The lock screw 108 includes a fastening tool engaging structure 152 at a first end portion 154 thereof and an upper saddle receiving structure 156 at a second end portion 158 thereof. A hex socket is a preferred embodiment of the fastening tool engaging structure 152.

As best shown in FIGS. 2 and 6, the lock screw threads 150 are cupped upwardly toward the first end portion 154 of the lock screw 108. As best shown in FIG. 2, the clamping body threads 124 are cupped upwardly toward the first end portion 112 of the clamping body 102. The clamping body threads 124 include spaced apart load carrying surfaces 156, 158 and a peripheral surface 160 extending therebetween, as shown in FIG. 2. Similarly, as best shown in FIGS. 5 and 6, the lock screw threads 150 include spaced apart load carrying surfaces 162, 164 and a peripheral surface 166 extending therebetween. More specifically, with respect to the cupped thread configuration, the load carrying surfaces 156, 158 of the clamping body 102 are cupped upwardly toward the first end portion 112 of the clamping body 102 and the load carrying surfaces i 62, 164 of the lock screw 108 are cupped upwardly toward the first end portion of the lock screw 108.

The cupped configuration of the lock screw threads 150 and the clamping body threads 124 advantageously enhance stability of the upstanding leg portions 119 when force is exerted thereon by the lock screw 108. Tightening of the lock screw 108 with the spine rod 133 disposed within the spine rode receiving channel 118 results in forces being exerted by the lock screw on the upstanding leg portions 119. Such force is exerted between the lock screw threads 150 and the clamping body threads 124. As such, with non-cupped threads, this force can cause the upstanding leg portions 119 to separate (i.e., splay apart), thereby leading to slipping, stripping, etc of the lock screw threads 150 with respect to the clamping body threads 124. The cupped configuration of the lock screw threads 150 and the clamping body threads 124 as disclosed herein advantageously causes the upstanding leg portions 119 to be drawn together when force is exerted on the upstanding leg portions 119 by the lock screw 108. Accordingly, a pedicle screw apparatus configured with cupped lock screw threads and the clamping body threads as disclosed herein provide for a superior interface between a clamping body and lock screw thereof and provide for superior structural robustness of upstanding leg portions thereof with the lock screw tightened in place.

Referring now to FIGS. 2, 6, 7 and 8, the upper saddle 110 is engaged at a first end portion 168 thereof with the upper saddle receiving structure 156 of the lock screw 108. The upper saddle 110 is engaged with the upper saddle receiving structure 156 in a manner allowing the upper saddle 110 to rotate about a centerline axis of the lock screw 108. As shown, in one embodiment, the upper saddle receiving structure 156 includes a passage 170 through which a mounting post 172 of the upper saddle extends, thus allowing rotation therebetween.

Figure 7:
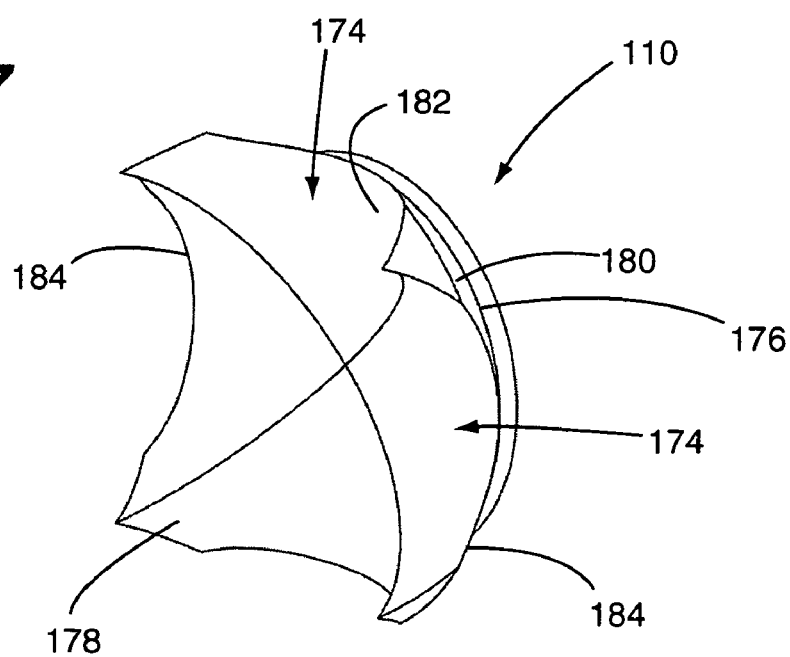
FIG. 7 is a perspective view showing a lower surface of an upper saddle for a pedicle screw apparatus in accordance with an embodiment of the present invention.

Perpendicularly intersecting spine rod receiving channels 174 extend through a spine rod engaging portion 176 of the upper saddle 110, as best shown in FIG. 7. The perpendicularly intersecting configuration of the spine rod receiving channels 174 is configured such that an outwardly-extending spine rod engaging structure 178 is provided between adjacent ones of the spine rod receiving channels 174. It is disclosed herein that one function of the spine rod engaging structure 178 is to align the upper saddle 110 to the spine rod 133. In the case where one of the spine rod receiving channels 174 is not fully aligned with a longitudinal axis of the spine rod 133, contact of the spine rod 133 by one of the spine rod engaging structure 178 causes rotation of the upper saddle 110 with respect to the spine rod 133 in response to bringing the upper saddle 110 into contact with the spine rod 133. As such, the upper saddle 110 will seek alignment (i.e., self aligning) with the spine rod 133 as the upper saddle is brought into further contact with the spine rod 133.

Figure 8:
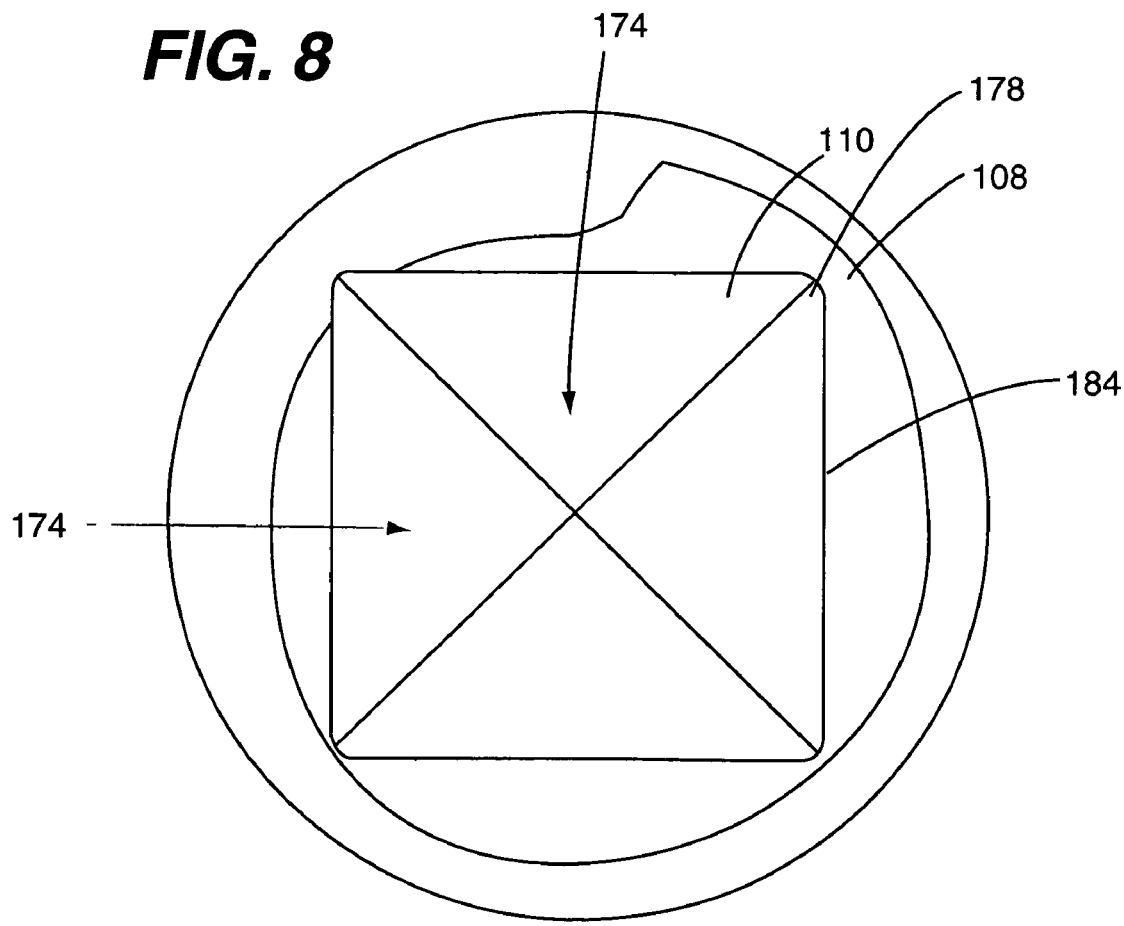
FIG. 8 is a cross sectional view taken along the line 8-8 in FIG. 7.

As best shown in FIG. 7, an upper surface 180 and a lower surface 182 of each spine rod engaging structure 178 are acutely angled with respect to each other and a channel edge 184 defined between the upper and lower surfaces 180, 182 is sharply pointed. Furthermore, the upper surface 180 of each spine rod engaging structure 178 is downwardly contoured such that a thickness of each spine rod engaging structure 178 is thinnest at a tip portion 184 thereof. The spine rod engaging portion 176 has a generally square end view profile such that the channel edge 184 defined between the upper and lower surfaces 180, 182 are generally straight in the end view (FIG. 8). The sharply pointed configuration advantageously serves to mechanically lock (i.e., engage) the upper saddle into position on a respective spine rod, thus preventing unintentional movement therebetween. Similarly, the downwardly contoured configuration of the upper surface 180 of the spine rod engaging structures 178, and the overall configuration of the upper saddle 110, serves to allow controlled deformation of the spine rod engaging structures 178. Such controlled deformation further promotes mechanically locking of the upper saddle in position on the respective spine rod (i.e., through the sharply pointed channel edge 184 biting into the surface of the spine rod), thus preventing unintentional movement therebetween.

In the preceding detailed description, reference has been made to the accompanying drawings that form a part hereof, and in which are shown by way of illustration specific embodiments in which the present invention may be practiced. These embodiments, and certain variants thereof, have been described in sufficient detail to enable those skilled in the art to practice embodiments of the present invention. It is to be understood that other suitable embodiments may be utilized and that logical, mechanical, chemical and electrical changes may be made without departing from the spirit or scope of such inventive disclosures. To avoid unnecessary detail, the description omits certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A lock screw assembly for securing a spine rod within a spine rod receiving body of a pedicle screw assembly, comprising:

a lock screw including a fastening tool engaging structure at a first end portion thereof and an upper saddle receiving structure at a second end portion thereof, wherein the upper saddle receiving structure includes a passage within an end face at the second end portion of the lock screw, wherein threads are provided on an exterior surface of the lock screw extend at least partially between the first and second end portions thereof; and an upper saddle having a mounting post extending from a top portion thereof and engaged within the passage within the end face at the second end portion of the lock screw for enabling the upper saddle to rotate with respect to the lock screw about a centerline axis of the lock screw, wherein a plurality of intersecting spine rod receiving channels extend through a spine rod engaging portion of the upper saddle in a manner such that an outwardly-extending spine rod engaging structure is provided between adjacent ones of said spine rod receiving channels, wherein a first one of said spine rod receiving channels extends substantially perpendicular to a second one of said spine rod receiving channels, wherein a longitudinal axis of the mounting post extends through a longitudinal centerline axis of each one of the intersecting spine rod receiving channels, wherein an upper surface of each spine rod engaging structure is downwardly contoured with respect to a lower surface of a respective spine rod engaging structure, wherein said upper and lower surfaces of each spine rod engaging structure are acutely angled with respect to each other, and wherein the upper surface of each spine rod engaging structure intersects a lower surface of the respective spine rod engaging structure to jointly define opposing sharply pointed channel edges of each one of said spine rod receiving channels.

2. The lock screw assembly of claim 1 wherein:

adjacent ones of the sharply pointed channel edges terminate into the outwardly-extending spine rod engaging structure located therebetween; and the contoured upper surface of each outwardly-extending spine rod engaging structure intersects the contoured upper surface of each adjacent outwardly-extending spine rod engaging structure.

3. The lock screw assembly of claim 1 wherein the contoured upper surface of each outwardly-extending spine rod engaging structure intersects the contoured upper surface of each adjacent outwardly-extending spine rod engaging structure.

\* \* \* \* \*